(12) United States Patent
Resconi et al.

(10) Patent No.: US 6,844,288 B2
(45) Date of Patent: Jan. 18, 2005

(54) PROCESS FOR THE PREPARATION OF LIGANDS FOR METALLOGENE CATALYSTS

(75) Inventors: Luigi Resconi, Ferrara (IT); Davide Balboni, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/309,509

(22) Filed: Dec. 4, 2002

(65) Prior Publication Data

US 2003/0158356 A1 Aug. 21, 2003

Related U.S. Application Data

(60) Continuation of application No. 10/140,469, filed on May 6, 2002, now abandoned, which is a division of application No. 09/486,881, filed as application No. PCT/EP99/04548 on Jul. 1, 1999, now Pat. No. 6,423,796.

(30) Foreign Application Priority Data

Jul. 2, 1998 (EP) .......................................... 98202226

(51) Int. Cl.$^7$ ................................................. C08F 4/42
(52) U.S. Cl. ...................... 502/152; 502/103; 526/160; 526/943; 526/127; 526/132; 526/133; 526/134; 526/351; 526/348; 556/53
(58) Field of Search ............................... 502/152, 103; 526/160, 943, 127, 132, 133, 134, 351, 348; 556/53

(56) References Cited

U.S. PATENT DOCUMENTS

| 4,522,982 | A | | 6/1985 | Ewen .......................... 525/240 |
| 5,053,478 | A | * | 10/1991 | Moore et al. ................ 528/125 |
| 5,504,169 | A | | 4/1996 | Canich ........................ 526/127 |
| 5,516,848 | A | | 5/1996 | Canich et al. ............... 525/240 |
| 5,539,056 | A | | 7/1996 | Yang et al. .................. 525/240 |
| 5,672,668 | A | | 9/1997 | Winter et al. ................ 526/127 |
| 5,693,836 | A | | 12/1997 | Winter et al. .................. 556/11 |
| 5,789,332 | A | | 8/1998 | Kutschera et al. .......... 502/106 |
| 6,028,152 | A | | 2/2000 | Winter et al. ................ 526/160 |
| 6,197,902 | B1 | | 3/2001 | Dolle et al. .................. 526/160 |
| 6,225,425 | B1 | | 5/2001 | Dolle et al. .................. 526/127 |

FOREIGN PATENT DOCUMENTS

| EP | 0399347 | 11/1990 | .......... C08F/10/00 |
| EP | 0584609 | 3/1994 | .......... C08F/4/602 |
| EP | 0604917 | 7/1994 | .......... C08F/110/06 |
| EP | 0633272 | 1/1995 | .......... C08F/10/02 |
| EP | 0693506 | 1/1996 | .......... C08F/110/06 |
| EP | 0722949 | 7/1996 | .......... C07F/17/00 |
| EP | 0722950 | 7/1996 | .......... C07F/17/00 |
| WO | 9200333 | 1/1992 | ............. C08F/4/76 |
| WO | 9500562 | 1/1995 | .......... C08F/10/00 |
| WO | 9525757 | 9/1995 | .......... C08F/10/06 |
| WO | 9526369 | 10/1995 | .......... C08F/10/00 |
| WO | 9532995 | 12/1995 | .......... C08F/10/00 |
| WO | WO 96/22995 | * 8/1996 | |
| WO | 9622995 | 8/1996 | .......... C07F/17/00 |
| WO | 9623838 | 8/1996 | .......... C08L/23/10 |
| WO | 9843931 | 10/1998 | .......... C07C/13/28 |
| WO | 9921896 | 5/1999 | .......... C08F/4/642 |
| WO | 9921899 | 5/1999 | .......... C08F/10/02 |

OTHER PUBLICATIONS

Nifant'ev et al., "General Synthetic Route to Substituted Bis(cyclopentadienyl)– and Bis(indenyl)methanes", Synthesis, p. 469–474 (1997).*

James C. Randall, "A Review of High Resolution Liquid $^{13}$Carbon Nuclear Magnetic Resonance Characterizations of Ethylene–Based Polymers", Macromol. Chem. Phys., C29(2&3), (1989) 201–317.

C. J. Carman et al., "Monomer Sequence Distribution in Ethylene–Propylene Rubber Measured by $^{13}$C NMR 3. Use of Reaction Probability Model", Macromolecules, vol. 10, No. 3, (1977) 536–44.

Ilya E. Nifantev et al., "General synthetic route to substituted bis(cyclopentadienyl)– and bis(indenyl)methanes", Synthesis (1997), (4), 469–74.

* cited by examiner

*Primary Examiner*—Ling-Siu Choi

(57) ABSTRACT

A process for the preparation of ligands for metallocene catalysts used in the production of amorphous polymers of alpha-olefins having high molecular weight and narrow molecular weight distributions, in which the isotactic sequences are more abundant than the syndiotactic ones.

10 Claims, 2 Drawing Sheets

FIG. 1  Magnitude: 45000

Magnitude: 45000

PROCESS FOR THE PREPARATION OF LIGANDS FOR METALLOGENE CATALYSTS

CROSS-REFERENCE TO RELATED APPLICATIONS

This application is a continuation of application Ser. No. 10/140,469, filed May 6, 2002, now abandoned which is a divisional of application Ser. No. 09/486,881, filed on Mar. 2, 2000, now U.S. Pat. No. 6,423,796 which is a national phase filing under 35 U.S.C. §371 of International Application No. PCT/EP99/04548 filed Jul. 1, 1999, which claims priority to EP Application No. 98202226.1 filed Jul. 2, 1998. The entire contents of application Ser. No. 10/140,469, application Ser. No. 09/486,881, International Application No. PCT/EP99/04548 and EP Application No. 98202226.1, each as filed, are incorporated herein by reference.

The present invention relates to a process for the preparation of substantially amorphous polymers of alpha-olefins. In particular, the present invention relates to a process for the preparation of substantially amorphous homo- and copolymers of propylene and compositions containing them together with isotactic polypropylene. The present invention relates also to a convenient process for the preparation of indenyl compounds useful for the preparation of metallocenes, which are used in the process for the preparation of substantially amorphous polymers of alpha-olefins.

Products of the propylene homopolymerization can be either crystalline or amorphous. Whereas the polypropylene having isotactic or syndiotactic structure is crystalline, the polypropylene having essentially atactic structure is amorphous.

Amorphous polypropylene finds applications as a component in hot melt adhesives, paper coatings and as a bitumen additive. Generally, it can be obtained as a side product from the preparation of isotactic polypropylene in the presence of heterogeneous Ziegler-Natta type catalysts. This product, however, has moderate molecular weight, broad molecular weight distribution, and contains some residual cristallinity. Moreover, the separation of the fraction of amorphous polypropylene from the remainder product involves an additional step of separation by means of solvents.

For use in a wider range of applications, notably in blends with crystalline polypropylene for PVC replacement, amorphous polypropylene having high molecular weight is required.

More recently, by polymerizing propylene in the presence of particular metallocene catalysts, amorphous polymers of propylene endowed with high molecular weights and a narrow molecular weight distribution have been obtained.

European patent application 604 917, for example, describes amorphous propylene polymers obtained in the presence of bridged bis-fluorenyl metallocenes. The structure of the polymers is substantially atactic, with the syndiotactic dyads being more numerous than the isotactic dyads.

In International application WO 95/00562 it is described a process for producing amorphous poly-alpha-olefins with a monocyclopentadienyl transition metal catalyst system. Both low and high molecular weight polymers can be obtained, with narrow molecular weight distributions. As for the polymers described in EP-A-604,917, also in this case the syndiotactic dyads are more abundant than the isotactic dyads.

These amorphous polymers of propylene find interesting applications in blends with cristalline polyolefins.

In International application WO 96/23838, for instance, there are described blends of high molecular weight amorphous polypropylene with lower molecular weight isotactic polypropylene. The amorphous polypropylene, which are produced by using the same catalyst as in WO95/00562, have more syndiotactic than isotactic dyads.

It would be desirable to make available amorphous alpha-olefin polymers endowed with high molecular weights and narrow molecular weight distributions, which are more miscible with isotactic poly-alpha-olefins. It would also be desirable to provide amorphous alpha-olefin polymers with improved elastomeric properties.

In European patent application EP-A-0 693 506 the preparation of substantially amorphous polymers of propylene in the presence of unbridged bis-indenyl or bis-4,5,6,7-tetrahydroindenyl compounds substituted in the 2-position on the indenyl or tetrahyroindenyl groups is described. In these polymers, the isotactic dyads are more numerous than the syndiotactic dyads. However, when the polymerization is carried out at temperatures of industrial interest, polymers of propylene endowed with low molecular weight are obtained.

In European patent application EP-A-0 584 609 it is described the preparation of polypropylene by means of a metallocene compound, which is used as a mixture of its racemic and meso isomeric form. The obtained polypropylene compositions contain fractions of amorphous and isotactic polypropylene. The miscibility of those fractions can still be improved.

U.S. Pat. No. 5,516,848 and U.S. Pat. No. 5,539,056 relate to the in situ preparation of polypropylene blends comprising high molecular weight amorphous polypropylene with lower molecular weight isotactic polypropylene. It is mentioned that blends containing low molecular weight amorphous polypropylene with high molecular weight isotactic polypropylene have poor elastic recovery properties, due to the stiffness of the isotactic polypropylene.

It has been surprisingly found that it is possible, operating at conditions of industrial interest, to prepare amorphous polymers of alpha-olefins having high molecular weights, narrow molecular weight distribution, with a predominance of isotactic dyads, by carrying out the polymerization reaction in the presence of metallocene catalysts comprising a particular substituted, single-atom-bridged, bis-indenyl compound.

Therefore, the present invention provides a process for the preparation of polymers of alpha-olefins, particularly of propylene, in the presence of a catalyst comprising the product obtainable by contacting:

(A) a metallocene compound in the racemic form of the formula (I):

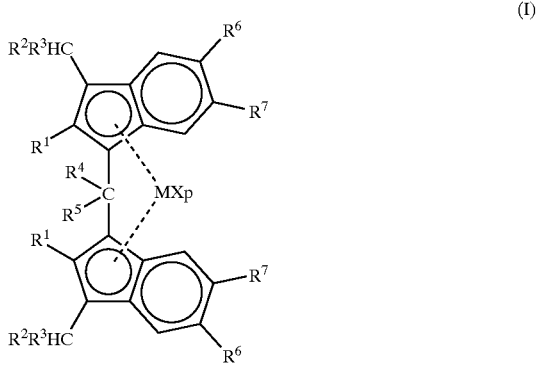

wherein substituents $R^1$ are hydrogen atoms;

$R^2$ and $R^3$ are, independently from each other, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms;

or where $R^2$ and $R^3$ can be joined together to form a 4 to 6 membered ring or a 6 to 20 fused ring system;

$R^4$ and $R^5$, same or different, are hydrogen atoms or —$CHR^8R^9$ groups;

$R^4$ and $R^5$ can form a ring having 3 to 8 carbon atoms, which can contain hetero atoms;

the $R^8$ and $R^9$ substituents, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, which can form a ring having 3 to 8 carbon atoms which can contain hetero atoms;

the $R^6$ and $R^7$ substituents, same or different, are hydrogen, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms; and optionally two adjacent $R^6$ and $R^7$ substituents can form a ring comprising from 5 to 8 carbon atoms;

M is a transition metal selected from those belonging to group 3, 4, 5, 6 or to the lanthanide or actinide groups in the Periodic Table of the Elements (new IUPAC version), X, same or different, is a monoanionic ligand, such as a hydrogen atom, a halogen atom, a $R^{10}$, $OR^{10}$, $OSO_2CF_3$, $OCOR^{10}$, $SR^{10}$, $NR^{10}_2$ or $PR^{10}_2$ group, wherein the substituents $R^{10}$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-alkylaryl radical, optionally containing silicon or germanium atoms;

p is an integer from 0 to 3, p being equal to the oxidation state of the metal M minus two; and (B) an alumoxane and/or a compound capable of forming an alkyl metallocene cation.

In the metallocene of formula (I) the transition metal M is preferably selected from titanium, zirconium and hafnium.

More preferably, the transition metal M is zirconium.

The X substituents are preferably chlorine atoms or methyl groups.

The $R^6$ and $R^7$ substituents are preferably hydrogen atoms.

Non-limiting examples of metallocene compounds of formula (I) suitable for use in the process of the invention are:

methylene-bis(3-isopropyl-indenyl)zirconium dichloride and dimethyl;
isopropylidene-bis(3-isopropyl-indenyl)zirconium dichloride and dimethyl;
cyclopentylidene-bis(3-isopropyl-indenyl)zirconium dichloride and dimethyl;
cyclohexylidene-bis(3-isopropyl-indenyl)zirconium dichloride and dimethyl;
methylene-bis[3-(1-methylpropyl)-indenyl]zirconium dichloride and dimethyl;
isopropylidene-bis[3-(1-methylpropyl)-indenyl]zirconium dichloride and dimethyl;
cyclopentylidene-bis[3-(1-methylpropyl)-indenyl]zirconium dichloride and dimethyl;
cyclohexylidene-bis[3-(1-methylpropyl)-indenyl]zirconium dichloride and dimethyl;
methylene-bis[3-(1-methylbutyl)-indenyl]zirconium dichloride and dimethyl;
isopropylidene-bis[3-(1-methylbutyl)-indenyl]zirconium dichloride and dimethyl;
cyclopentylidene-bis[3-(1-methylbutyl)-indenyl]zirconium dichloride and dimethyl;
cyclohexylidene-bis[3(1-methylbutyl)-indenyl]zirconium dichloride and dimethyl;
methylene-bis[3-(1-phenylethyl)indenyl]zirconium dichloride and dimethyl;
isopropylidene-bis[3-(1-phenylethyl)indenyl]zirconium dichloride and dimethyl;
cyclopentylidene-bis[3-(1-phenylethyl)indenyl]zirconium dichloride and dimethyl;
cyclohexylidene-bis[3-(1-phenylethyl)indenyl]zirconium dichloride and dimethyl;
methylene-bis(3-diphenylmethyl-indenyl)zirconium dichloride and dimethyl;
isopropylidene-bis(3-diphenylmethyl-indenyl)zirconium dichloride and dimethyl;
cyclopentylidene-bis(3-diphenylmethyl-indenyl)zirconium dichloride and dimethyl;
cyclohexylidene-bis(3-diphenylmethyl-indenyl)zirconium dichloride and dimethyl;
methylene-bis[3-(1-cyclohexyl)methylindenyl]zirconium dichloride and dimethyl;
isopropylidene-bis[3-(1-cyclohexyl)methylindenyl]zirconium dichloride and dimethyl;
cyclopentylidene-bis[3-(1-cyclohexyl)methylindenyl]zirconium dichloride and dimethyl;
cyclohexylidene-bis[3-(1-cyclohexyl)methylindenyl]zirconium dichloride and dimethyl;
methylene-bis(3-biscyclohexylmethyl-indenyl)zirconium dichloride and dimethyl;
isopropylidene-bis(3-biscyclohexylmethyl-indenyl)zirconium dichloride and dimethyl;
cyclopentylidene-bis(3-biscyclohexylmethyl-indenyl)zirconium dichloride and dimethyl;
cyclohexylidene-bis(3-biscyclohexylmethyl-indenyl)zirconium dichloride and dimethyl;
methylene-bis(3-biscyclopentylmethyl-indenyl)zirconium dichloride and dimethyl;
isopropylidene-bis(3-biscyclopentylmethyl-indenyl)zirconium dichloride and dimethyl;
cyclopentylidene-bis(3-biscyclopentylmethyl-indenyl)zirconium dichloride and dimethyl;
cyclohexylidene-bis(3-biscyclopentylmethyl-indenyl)zirconium dichloride and dimethyl;
methylene-bis(3-biscyclopropylmethyl-indenyl)zirconium dichloride and di methyl;
isopropylidene-bis(3-biscyclopropylmethyl-indenyl)zirconium dichloride and dimethyl;
cyclopentylidene-bis(3-biscyclopropylmethyl-indenyl)zirconium dichloride and dimethyl;
cyclohexylidene-bis(3-biscyclopropylmethyl-indenyl)zirconium dichloride and dimethyl;
methylene-bis(3-cyclohexyl-indenyl)zirconium dichloride and dimethyl;
isopropylidene-bis(3-cyclohexyl-indenyl)zirconium dichloride and dimethyl;
cyclopentylidene-bis(3-cyclohexyl-indenyl)zirconium dichloride and dimethyl;
cyclohexylidene-bis(3-cyclohexyl-indenyl)zirconium dichloride and dimethyl;
methylene-bis(3-cyclopentyl-indenyl)zirconium dichloride and dimethyl;
isopropylidene-bis(3-cyclopentyl-indenyl)zirconium dichloride and dimethyl;

cyclopentylidene-bis(3-cyclopentyl-indenyl)zirconium dichloride and dimethyl;
cyclohexylidene-bis(3-cyclopentyl-indenyl)zirconium dichloride and dimethyl;
methylene-bis(3-cyclopropyl-indenyl)zirconium dichloride and dimethyl;
isopropylidene-bis(3-cyclopropyl-indenyl)zirconium dichloride and dimethyl;
cyclopentylidene-bis(3-cyclopropyl-indenyl)zirconium dichloride and dimethyl;
cyclohexylidene-bis(3-cyclopropyl-indenyl)zirconium dichloride and dimethyl;
methylene-bis(3-cycloheptyl-indenyl)zirconium dichloride and dimethyl;
isopropylidene-bis(3-cycloheptyl-indenyl)zirconium dichloride and dimethyl;
cyclopentylidene-bis(3-cycloheptyl-indenyl)zirconium dichloride and dimethyl;
cyclohexylidene-bis(3-cycloheptyl-indenyl)zirconium dichloride and dimethyl;
methylene-bis(3-norbornyl-indenyl)zirconium dichloride and dimethyl;
isopropylidene-bis(3-norbornyl-indenyl)zirconium dichloride and dimethyl;
cyclopentylidene-bis(3-norbornyl-indenyl)zirconium dichloride and dimethyl;
cyclohexylidene-bis(3-norbornyl-indenyl)zirconium dichloride and dimethyl.

Most preferably the metallocene compounds of formula (I) are methylene-bis(3-isopropyl-indenyl)zirconium dichloride and isopropylidene-bis(3-isopropyl-indenyl)zirconium dichloride.

The preparation of the ligands for the metallocenes of formula (I) can be carried out by different methods. A particularly suitable method for preparing the ligands for the metallocenes of formula (I) wherein $R^4$ and $R^5$ are hydrogen atoms is reported in WO 98/43931. A method for preparing the ligands for the metallocenes of formula (I) wherein at least one of the substituents $R^4$ and $R^5$ is different from hydrogen atoms is described in EP-A 0 722 949 and EP-A 0 722 950. The synthetic routes described therein, however, are rather complicated and involve the use of the toxic and expensive dimethoxyethane (DME). Further, since the above synthesis requires the use of excessive hydroxides, the disposal of not consumed hydroxides involves additional environmental protection measures.

According to a further aspect of the present invention, it is provided a process for the preparation of a compound of formula (II):

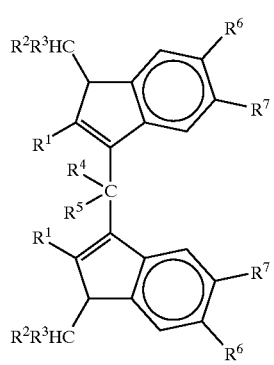

(II)

and/or its double bond isomers, wherein $R^1$, $R^2$, $R^3$, $R^4$, $R^5$, $R^6$ and $R^7$ are defined as above; comprising the following steps:

a) contacting a compound of formula (III):

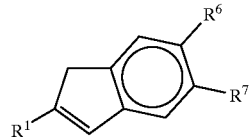

(III)

and/or its double bound isomer,
wherein $R^1$, $R^6$ and $R^7$ have the meaning as described above,
with a base selected from the group consisting of alkali and earth alkali metal hydroxides or alkoxides in the presence of an oxygen containing solvent;

b) treating the obtained corresponding anionic form with a compound of general formula $R^4R^5CO$, wherein $R^4$ and $R^5$ have the same meaning as defined above, in order to obtain a compound of the formula (IV):

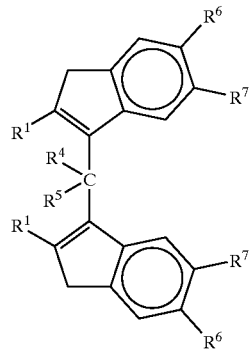

(IV)

and/or its double bound isomers;
wherein $R^1$, $R^4$, $R^5$, $R^6$ and $R^7$ have the meaning as above mentioned;

c) contacting the compound of formula (IV) with a base, wherein the molar ratio between the base and the compound of formula (IV) is equal to or greater than 2;

d) treating the corresponding di-anionic form of formula (IV) with a compound (V) of formula $CHR^2R^3L$, $R^2$ and $R^3$ being as defined above and L is a halogen atom selected from the group 17 of the Periodic Table of the Elements (new IUPAC version), wherein the molar ratio between the compound (V) and the corresponding di-anionic form of formula (IV) is equal to or greater than 2.

The bases, which may be used in step a) are preferably sodium or potassium hydroxide. The molar ratio between said base and the indenyl compound of formula (III) can vary over a wide range. The process of the present invention has the advantage that the base can be used in less than stoichiometric amounts. The molar ratio between said base and said indenyl compound of formula (III) preferably ranges from a catalytic amount to 1. More preferably from 0.01 to 1, and even more preferably from 0.1 to 1.

Preferably, the oxygen containing solvent used in step a) is dimethylsulfoxide (DMSO) or 1-Me-2-pyrrolidinone.

The compound of general formula $R^4R^5CO$, which is used in the above step a) for introducing the bridge between two indenyl moieties of general formula (III), can be, for instance, formaldehyde, formaline, acetone, cyclohexanone or cyclopentanone.

The base used in step c) is selected from alkali and earth alkali metal hydroxides, organic lithium compounds and metallic sodium or potassium, preferably the base is buthyllithium. The contact treatment of compound of general formula (IV) and the base, such as buthyllithium, can be carried out in a solvent such as THF or diethylether.

In the process according to the present invention L is selected from chlorine, bromine, iodine and fluorine, preferably L is bromine. Non-limiting examples of compounds of formula $CHR^2R^3L$ are, for instance, 2-bromopropane, 2-bromohexane or diphenylbromomethane. The temperature in the reaction medium can vary in dependence of the solvent, the nature and the quantity of the used compounds and is generally in the range of between room temperature and reflux temperature of the solvent used.

The purification of the ligand of formula (II) can be carried out according to general known methods, such as distillation or filtration.

Non-limiting examples of compounds of formula (II) are:

1,1-bis(3-isopropyl-indenyl)methane;
2,2-bis(3-isopropyl-indenyl)propane;
1,1-bis(3-isopropyl-indenyl)cyclopentane;
1,1-bis(3-isopropyl-indenyl)cyclohexane;
1,1-bis[3-(1-methylpropyl)-indenyl]methane;
2,2-bis[3-(1-methylpropyl)-indenyl]propane;
1,1-bis[3-(1-methylpropyl)-indenyl]cyclopentane;
1,1-bis[3-(1-methylpropyl)-indenyl]cyclohexane;
1,1-bis[3-(1-methylbutyl)-indenyl]methane;
2,2-bis[3-(1-methylbutyl)-indenyl]propane;
1,1-bis[3-(1-methylbutyl)-indenyl]cyclopentane;
1,1-bis[3-(1-methylbutyl)-indenyl]cyclohexane;
1,1-bis[3-(1-phenylethyl)indenyl]methane;
2,2-bis[3-(1-phenylethyl)indenyl]propane;
1,1-bis[3-(1-phenylethyl)indenyl]cyclopentane;
1,1-bis[3-(1-phenylethyl)indenyl]cyclohexane;
1,1-bis(3-diphenylmethyl-indenyl)methane;
2,2-bis(3-diphenylmethyl-indenyl)propane;
1,1-bis(3-diphenylmethyl-indenyl)cyclopentane;
1,1-bis(3-diphenylmethyl-indenyl)cyclohexane;
1,1-bis[3-(1-cyclohexyl)methylindenyl]methane;
2,2-bis[3-(1-cyclohexyl)methylindenyl]propane;
1,1-bis[3-(1-cyclohexyl)methylindenyl]cyclopentane;
1,1-bis[3-(1-cyclohexyl)methylindenyl]cyclohexane;
1,1-bis(3-biscyclohexylmethyl-indenyl)methane;
2,2-bis(3-biscyclohexylmethyl-indenyl)propane;
1,1-bis(3-biscyclohexylmethyl-indenyl)cyclopentane;
1,1-bis(3-biscyclohexylmethyl-indenyl)cyclohexane;
1,1-bis(3-biscyclopentylmethyl-indenyl)methane;
2,2-bis(3-biscyclopentylmethyl-indenyl)propane;
1,1-bis(3-biscyclopentylmethyl-indenyl)cyclopentane;
1,1-bis(3-biscyclopentylmethyl-indenyl)cyclohexane;
1,1-bis(3-biscyclopropylmethyl-indenyl)methane;
2,2-bis(3-biscyclopropylmethyl-indenyl)propane;
1,1-bis(3-biscyclopropylmethyl-indenyl)cyclopentane;
1,1-bis(3-biscyclopropylmethyl-indenyl)cyclohexane;
1,1-bis(3-cyclohexyl-indenyl)methane;
2,2-bis(3-cyclohexyl-indenyl)propane;
1,1-bis(3-cyclohexyl-indenyl)cyclopentane;
1,1-bis(3-cyclohexyl-indenyl)cyclohexane;
1,1-bis(3-cyclopentyl-indenyl)methane;
2,2-bis(3-cyclopentyl-indenyl)propane;
1,1-bis(3-cyclopentyl-indenyl)cyclopentane;
1,1-bis(3-cyclopentyl-indenyl)cyclohexane;
1,1-bis(3-cyclopropyl-indenyl)methane;
2,2-bis(3-cyclopropyl-indenyl)propane;
1,1-bis(3-cyclopropyl-indenyl)cyclopentane;
1,1-bis(3-cyclopropyl-indenyl)cyclohexane;
1,1-bis(3-cycloheptyl-indenyl)methane;
2,2-bis(3-cycloheptyl-indenyl)propane;
1,1-bis(3-cycloheptyl-indenyl)cyclopentane;
1,1-bis(3-cycloheptyl-indenyl)cyclohexane;
1,1-bis(3-norbornyl-indenyl)methane;
2,2-bis(3-norbornyl-indenyl)propane;
1,1-bis(3-norbornyl-indenyl)cyclopentane;
1,1-bis(3-norbornyl-indenyl)cyclohexane.

Most preferably the compound of formula (II) is 2,2-bis(3-isopropyl-indenyl)propane. The metallocene compounds of formula (I) can be prepared by contacting the corresponding bis-indenyl ligands of formula (II) with a compound capable of forming a delocalized anion on the cyclopentadienyl ring, and with a compound of formula $M_{p+2}$, wherein M, X and p are defined as above.

In the case in which at least one substituent X in the metallocene compound of the formula (I) which is to be prepared is other than a halogen, it is necessary to substitute at least one substituent X in the metallocene obtained by at least one substituent X other than a halogen.

The reaction of substituting substituents X by substituents X other than a halogen is carried out using generally applied methods. For example, if the desired substituents X are alkyl groups, the metallocenes can be made to react with alkylmagnesium halides (Grignard reagents) or with alkyllithium compounds.

In the catalyst used in the process according to the invention, both the metallocene compound of the formula (I) and the alumoxane can be present as the product of the reaction with an organometallic aluminium compound of the formula $AlR^{11}_3$ or $Al_2R^{11}_6$, in which the $R^{11}$ substituents, same or different, are defined as the substituents $R^8$ or are halogen atoms.

The alumoxanes used in the process of the present invention may be obtained by reaction between water and an organometallic compound of aluminium of formula $AlR^{11}_3$ or $Al_2R^{11}_6$, in which the $R^{11}$ substituents, same or different, are defined as above, with the condition that at least one $R^{11}$ is different from halogen. The molar ratio between the aluminium and water is in the range of 1:1 and 100:1.

Non-limiting examples of aluminium compounds of the formula $AlR^{11}_3$ or $Al_2R^{11}_6$ are: $Al(Me)_3$, $Al(Et)_3$, $AlH(Et)_2$, $Al(iBu)_3$, $AlH(iBu)_2$, $Al(iHex)_3$, $Al(iOct)_3$, $AlH(iOct)_2$, $Al(C_6H_5)_3$, $Al(CH_2C_6H_5)_3$, $Al(CH_2CMe_3)_3$, $Al(CH_2SiMe_3)_3$, $Al(Me)_2iBu$, $Al(Me)_2Et$, $AlMe(Et)_2$, $AlMe(iBu)_2$, $Al(Me)_2iBu$, $Al(Me)_2Cl$, $Al(Et)_2Cl$, $AlEtCl_2$ and $Al_2(Et)_3Cl_3$, wherein Me=methyl, Et=ethyl, iBu=isobutyl, iHex=isohexyl, iOct=2,4,4-trimethyl-pentyl.

Particularly interesting aluminium compounds are those described in the European application No. 97203332.8 in which the alkyl groups have specific branched patterns. Non-limiting examples of aluminium compounds according to said European application are: tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethylbutyl)aluminium, tris(2-ethyl-3,3-dimethyl-pentyl) aluminium, tris(2-isopropyl-3,3-dimethyl-butyl)aluminium, tris(2-trimethylsilyl-propyl)aluminium, tris(2-methyl-3-phenyl-butyl)aluminium, tris(2ethyl-3-phenyl-butyl) aluminium, tris(2,3-dimethyl-3-phenyl-butyl)aluminium, as well as the corresponding compounds wherein one of the hydrocarbyl groups is replaced by an hydrogen atom, and those wherein one or two of the hydrocarbyl groups are replaced by an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminum (TDMBA) and tris(2,3,3-trimethylbutyl)aluminum (TTMBA) are preferred.

The alumoxanes used in the catalyst according to the invention are considered to be linear, branched or cyclic compounds containing at least one group of the type:

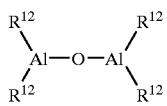

wherein the substituents $R^{12}$, same or different, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing hydrogen atoms, silicon or germanium atoms, or a —O—Al($R^{12}$)$_2$ group and, if appropriate, some substituents $R^{12}$ can be halogen atoms.

In particular, alumoxanes of the formula:

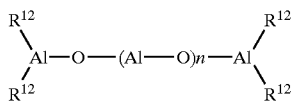

can be used in the case of linear compounds, wherein n is 0 or an integer of from 1 to 40 and the substituents $R^{12}$ are defined as above, or alumoxanes of the formula:

can be used in the case of cyclic compounds, wherein n is an integer of from 2 to 40 and the $R^{12}$ substituents are defined as above. The substituents $R^{12}$ are preferably ethyl, isobutyl or 2,4,4-trimethyl-pentyl groups. Examples of alumoxanes suitable for use according to the present invention are methylalumoxane (MAO), isobutylalumoxane (TIBAO), 2,4,4-trimethyl-pentylalumoxane (TIOAO), 2,3-dimethylbutylalumoxane (TDMBAO) and 2,3,3-trimethylbutylalumoxane (TTMBAO).

The catalyst for use in the process according to the invention can suitably be obtained by a process described in the European application No. 97203331.0 comprising the following steps:

(i) contacting the metallocene compound of the formula (I) with part of the described aluminium compound in the absence of water;
(ii) contacting part of the above described aluminium compound with water in the absence of the metallocene compound of the formula (I) and successively:
(iii) contacting the products obtained in steps (i) and (ii).

The part of aluminium compound used in each one of steps (i) and (ii) can consist of the same compound(s) or different compounds.

The molar ratio between the aluminium and the metal of the metallocene compound is in general comprised between 10:1 and 20000:1, and preferably between 100:1 and 5000:1.

Non-limiting examples of compounds able to form an alkylmetallocene cation are compounds of the formula $Y^+Z^-$, wherein $Y^+$ is a Brønsted acid, able to donate a proton and to react irreversibly with a substituent X of the compound of the formula (I), and $Z^-$ is a compatible anion which does not coordinate and which is able to stabilize the active catalytic species which results from the reaction of the two compounds and which is sufficiently labile to be displaceable by an olefin substrate. Preferably, the anion $Z^-$ consists of one or more boron atoms. More preferably, the anion $Z^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred. Moreover, compounds of the formula $BAr_3$ can conveniently be used. Compounds of this type are described, for example, in the published International patent application WO 92/00333.

The catalysts of the present invention can also be used on supports. This is achieved by depositing the metallocene compound (A) or the product of the reaction thereof with the component (B), or the component (B) and then the metallocene compound (A) on supports such as, for example, silica, alumina, magnesium halides, styrene/divinylbenzene copolymers, polyethylene or polypropylene.

A suitable class of supports, which can be used, is constituted by porous organic supports functionalized with groups having active hydrogen atoms. Particularly suitable are those in which the organic support is a partially crosslinked styrene polymer. Supports of this type are described in European application EP-633 272.

Another class of inert supports particularly suitable for use according to the invention is that of the olefin, particularly propylene, porous prepolymers described in International application WO 95/26369.

A further suitable class of inert supports for use according to the invention is that of the porous magnesium halides such as those described in International application WO 95/32995.

The solid compound thus obtained, in combination with the further addition of the alkylaluminium compound either as such or pre-reacted with water if necessary, can be usefully employed in the gas-phase polymerization.

By polymerizing propylene in the presence of the above particular metallocenes it is possible to obtain in high yields, at temperature of industrial interest (i.e. equal to or higher than 40° C.), amorphous polypropylene having high molecular weights.

The propylene polymerization process according to the invention can be carried out in the liquid phase in the presence or absence of an inert hydrocarbon solvent, or in the gas phase. The hydrocarbon solvent can either be aromatic such as toluene, or aliphatic such as propane, hexane, heptane, isobutane or cyclohexane.

Although the polymerization temperature and pressure is not critical, the polymerization of propylene is generally carried out at a temperature between 0° C. and 250° C., particularly between 20° C. and 150° C., and more particularly between 40° C. and 90° C. The polymerization pressure is generally comprised between 0.5 and 100 bar.

The lower the polymerization temperature, the higher are the resulting molecular weights of the polymers obtained.

The molecular weight of the polymers can be varied merely by changing the polymerization temperature, the type or the concentration of the catalytic components or by using molecular weight regulators such as hydrogen.

The polymerization yields depend on the purity of the metallocene compound of the catalyst. The metallocene compounds obtained by the process of the invention can therefore be used as such or can be subjected to purification treatments.

The components of the catalyst can be brought into contact each other before the polymerization. The pre-contact concentrations are generally between 1 and $10^{-8}$ mol/l for the metallocene component (A), while they are generally between 10 and $10^{-8}$ mol/l for the component (B). The pre-contact is generally effected in the presence of a hydrocarbon solvent and, if appropriate, of small quantities of monomer. In the pre-contact it is also possible to use a non-polymerizable olefin such as isobutene and 2-butene.

The propylene polymers obtainable with the process of the present invention may have a varying content of isotactic sequences. Generally, the percentage of the isotactic triads (mm) is in the range from 10 to 80, preferably from 25 to 50. Therefore, they can be from substantially amorphous to partially crystalline. Their melting enthalpy is generally lower than 70 J/g, preferably lower than 50 J/g, and most preferably lower than 20 J/g. Those polymers with the shortest isotactic sequences show no detectable melting enthalpy.

The structure of the above polymers of propylene is substantially atactic. Nevertheless, it is observed that the isotactic pentads (mmmm) appear to be more numerous than the syndiotactic pentads. Thus, the ratio of the isotactic pentads (mmmm) and the syndiotactic pentads (rrrr) satisfy the relation:

$(mmmm)/(rrrr) > 1.5$, and preferably $(mmmm)/(rrrr) \geq 2.0$.

The ratio of the pentads (mmmm) and the pentads (mmmr) satisfy the relation:

$(mmmm)/(mmmr) > 0.8$, and preferably $(mmmm)/(mmmr) > 0.9$, more preferably $(mmmm)/(mmmr) > 1.0$.

The tacticity of the polymeric chain, i.e. the distribution of the relative configuration of the tertiary carbons, is determined by $^{13}$C-NMR analysis.

The molecular weights of the above said propylene polymers can be quite high. Thus, the intrinsic viscosity can reach values of greater than 0.5 dl/g, even greater than 2 dl/g.

Further, the molecular weights of the propylene polymers are distributed over relatively limited ranges. The molecular weight distribution can be represented by the ratio $M_w/Mn$ which, for the present polymers, is generally lower than 4, preferably lower than 3.5 and, more preferably, lower than 3.

The molecular weight distribution can be varied by using mixtures of different metallocene compounds or by carrying out the polymerization in several stages which differ as to the polymerization temperature and/or the concentrations of the molecular weight regulators.

The structure of the above said propylene polymers appears to be very regioregular. In fact, according to the $^{13}$C-NMR, signals relating to sequences $(CH_2)_n$ wherein n=2 are not detectable. Generally, less than 2% and, preferably, less than 1% of the $CH_2$ groups are contained in sequences $(CH_2)_n$ wherein n=2.

The polymers of the invention are generally soluble in common solvents, such as, for instance, chloroform, diethylether, hexane, heptane, toluene and xylene.

The polymers of the invention are endowed with good elastomeric properties as well as with good optical properties, being quite transparent.

The polymers of the invention are transformable into shaped articles by conventional material processing, such as moulding, extrusion, injection etc.

The polymerization reaction according to the invention can be carried out in the presence of ethylene or of a $C_4$–$C_{10}$ alpha-olefin comonomer. It is thus possible to obtain substantially amorphous propylene copolymers endowed with a good distribution of the comonomer along the polypropylene chain.

Non-limiting examples of alpha-olefins which can be used as comonomers in the copolymers according to the present invention are ethylene, 1-butene, 1-pentene, 1-hexene, 4-methyl-1-pentene, 1-octene, 1-decene, 1-dodecene, styrene, 1,5-hexadiene and 1,7-octadiene.

The copolymers according to the present invention are characterized by a homogeneous distribution of the comonomer units within the polymeric chain.

A particular interesting embodiment of the present invention is constituted of a process for preparing copolymers of propylene with ethylene.

The analysis of the distribution of the comonomer units in the copolymers of the invention has been carried out by means of $^{13}$C-NMR spectroscopy. The assignments were carried out as described by Randall in Macromol.Chem.Phys.1989, 29, 201. The distribution of triads, in the case of propylene/ethylene, are calculated by the following relationship:

| PPP = $T_{\beta\beta}$ | EPE = $T_{\delta\delta}$ | EPP = $T_{\beta\delta}$ | PEP = $S_{\beta\beta}$ | PEE = $S_{\beta\delta}$ |
|---|---|---|---|---|
| | EEE = $0.5(S_{\delta\delta} + 0.5_{\gamma\delta})$ | | | | wherein PEP, EEP and EEE represent the sequence propylene/ethylene/propylene, ethylene/ethylene/propylene and ethylene/ethylene/ethylene, respectively, in the copolymer. For the NMR nomenclature, see J. Carmen, R. A. Harrington, C. E. Wilkes, Macromolecules, 10, 537 (1977). The values are normalised. The higher the number of isolated ethylene units in the polymeric chain, the more the values of the ratio PEP/(PEP+EEP+EEE) become closer to the unit.

Table 4 refers to propylene/ethylene copolymers obtained with a process according to the present invention.

In particular, in table 4 there are reported the ratios PEP/(PEP+EEP+EEE) as a function of the weight percentage of ethylene in the chain for propylene/ethylene copolymers obtained with a process according to the present invention, in the presence of the above reported metallocene compounds. The amounts of ethylene units being equal, the values of the ratio PEP/(PEP+EEP+EEE) for the copolymers of the invention are always higher than those for the copolymers obtained with metallocenes used in the comparative examples, reflecting the improved distribution of ethylene units in the chain.

In particular, the ratio PEP/(PEP+EEP+EEE) satisfies the following relationship:

$PEP/(PEP+EEP+EEE) \geq 0.75$ preferably:

$PEP/(PEP+EEP+EEE) \geq 0.85$ more preferably $PEP/(PEP+EEP+EEE) \geq 0.9$.

The copolymers of the present invention have intrinsic viscosity values (I.V.) generally higher than 0.5 dl/g and preferably higher than 0.6 dl/g.

As for the homopolymers, the copolymers of the present invention are generally endowed with a narrow molecular weight distribution. The ratio $M_w/M_n$ for the copolymers of the present invention is generally lower than 4, preferably lower than 3.5 and, more preferably, lower than 3.

The glass transition temperatures (Tg) of the copolymers according to the invention are generally well below 0° C., thus allowing the use of articles made thereof to be used at low temperatures.

The propylene polymers of the present invention are particularly suitable to prepare blends with isotactic polymers of alpha-olefins, in particular propylene.

Therefore, it is a further aspect of the present invention a thermoplastic composition comprising:

(A) 1 to 99% by weight of a propylene polymer optionally containing from 0.1 to 20% by moles of units deriving from an olefin of formula $CH_2=CHR$, R being hydrogen, a $C_2$–$C_{20}$-alkyl or a $C_6$–$C_{12}$-aryl group, having the following characteristics:

melting enthalpy<70 J/g;

the ratio of the pentads (mmmm)/(rrrr)>1.5; and the ratio of the pentads (mmmm)/(mmmr)≧0.8;

(B) 1 to 99% by weight of a propylene polymer, optionally containing from 0.1 to 20% by moles of units deriving from an olefin of formula $CH_2=CHR$, R being hydrogen, a $C_2$–$C_{20}$-alkyl or a $C_6$–$C_{12}$-aryl group, having the following characteristics:

melting enthalpy>70 J/g, and

% of isotactic dyads (m)–% of syndiotactic dyads (r)>0.

In the composition of the present invention the ratio of the quantities by weight of the components (A)/(B) is preferably comprised between 10:90 and 90:10. More preferably, the ratio of the quantities by weight of the components (A)/(B) is comprised between 30:70 and 70:30.

The structure of the above polymers of propylene used as component (A) is substantially atactic. Nevertheless, it is observed that the isotactic pentads (mmmm) appear to be more numerous than the syndiotactic pentads. Thus, the ratio of the isotactic pentads (mmmm) and the syndiotactic pentads (rrrr) satisfy the relation:

(mmmm)/(rrrr)>1.5, and preferably (mmmm)/(rrrr)≧2.0.

The ratio of the pentads (mmmm) and the pentads (mmmr) satisfy the relation:

(mmmm)/(mmmr)>0.8, and preferably (mmmm)/(mmmr)>0.9, more preferably (mmmm)/(mmmr)≧1.0.

The propylene polymers used as component (A) of the composition according to the present invention may have a varying content of isotactic sequences. Generally, the percentage of the isotactic triads % (mm) is in the range from 10 to 80, preferably from 25 to 50. Therefore, they can be from substantially amorphous to partially crystalline and their melting enthalpy is generally lower than 70 J/g, preferably lower than 50 J/g, and most preferably lower than 20 J/g. Those polymers with the shortest isotactic sequences show no detectable melting enthalpy. The molecular weights of the above said propylene polymers can be quite high. Thus, the intrinsic viscosity is generally greater than 0.5 dl/g, and can reach values greater than 2 dl/g. Further, the molecular weights of the propylene polymers used as component (A) of the composition according to the present invention are distributed over relatively limited ranges. The molecular weight distribution can be represented by the ratio $M_w/M_n$ which, for the present polymers, is generally lower than 4, preferably lower than 3.5 and, more preferably, lower than 3.

The structure of the above said propylene polymers, which is used as component (A) of the composition according to the present invention, appears to be very regioregular. In fact, according to the $^{13}$C-NMR, signals relating to sequences $(CH_2)_n$ wherein n=2 are not detectable. Generally, less than 2% and, preferably, less than 1% of the $CH_2$ groups are contained in sequences $(CH_2)_n$ wherein n=2.

The melting point of the isotactic polypropylene used as component (B) is generally between 110° C. and 160° C., and can even reach values above 160° C.

The molecular weight of the substantially isotactic polypropylene can be quite high. Thus, the intrinsic viscosity can reach values of greater than 1 dl/g, even greater than 2 dl/g. Preferably, the melting enthalpy of the isotactic polymer of propylene is >90 J/g. Examples of isotactic polymers of propylene for use as component (B) are commercial available isotactic polypropylene, which are produced by means of conventional titanium or vanadium based heterogenes Ziegler-Natta-type catalysts. Also can be used metallocene based isotactic polymers having the above described characteristics. Polymers made by means of metallocenes generally have narrow molecular weight distribution $M_w/M_n$, such as values of lower than 3.

In the above mentioned copolymers, which can be used under (A) and/or (B), the co-monomer can for instance, without any limitation, selected from ethylene, 1-butene, styrene, or cyclohexene.

The melting point of the isotactic propylene copolymers used under (B) is generally between 110° C. and 140° C. The fraction soluble in xylene at 25° C. is generally less than 10%.

The composition of the present invention may contain, as necessary, various additives, reinforcing agents and fillers, such as heat stabilizers, antioxidants, light stabilizers, antistatic agents, lubricants, nucleating agents, flame retardants, pigments or dyes, glass fiber, carbon fiber, calcium carbonate, calcium sulfate, barium sulfate, magnesium hydroxide, mica, talc, or clay.

The preparation of the present composition comprising the components (A) and (B) is not critical and can be carried out by a method commonly used in the preparation of conventional polypropylene compositions, wherein melt kneading is conducted with heating, using, for example, a kneader (e.g. kneader, Banbury, rolls) or a single-screw or twin-screw extruder.

The composition of the present invention can be processed in the same manner as conventional polypropylene compositions. They can be extruded, injection moulded, compression moulded, in order to obtain films, fibers, filaments sheets, fabric, wire and cable coatings. For instance, the composition according to the present invention can also be used for the preparation of low-temperature-heat-sealing film. Article, in particular films and sheets made of the compositions according to the present invention have excellent transparency. A further advantage of the compositions of the present invention is the resistance to blooming. Blooming can be a severe problem in soft polymeric compositions because it causes surface stickiness.

The miscibility of the composition of the components (A) and (B) of the present invention was evaluated by haze measurments (ASTM D1003) and Transmission Electron Micrograph (TEM) microstructures.

BRIEF DESCRIPTION OF THE FIGURES

The enhanced miscibility of the substantially amorphous polymer of propylene with isotactic polypropylene is illustrated by means of the following FIGS. 1 and 2, which are Transmission Electron Micrographs (TEM).

Figure 1:
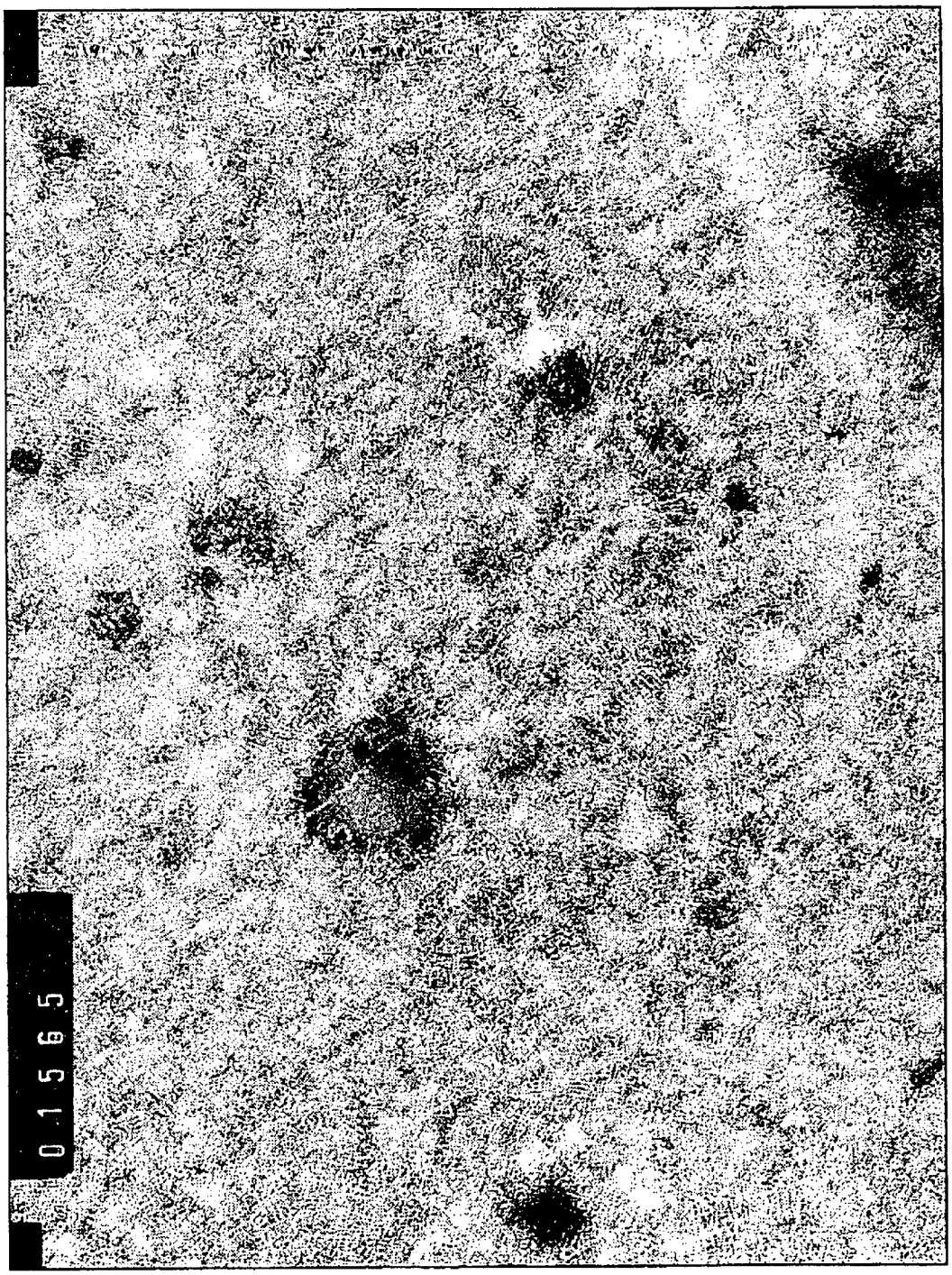
FIG. 1 is a TEM (45000×) of a composition according to the present invention as described in Example 14, comprising a substantially amorphous polypropylene made by rac—Me$_2$C(3-iPr-Ind)$_2$ZrCl$_2$ and a commercial substantial isotactic polypropylene, Moplen Q30P (I.V.:2.6 dl/g) (50/50 wt. %). The microstructure shows that the composition according to the present invention is substantially homogeneous.
Figure 2:
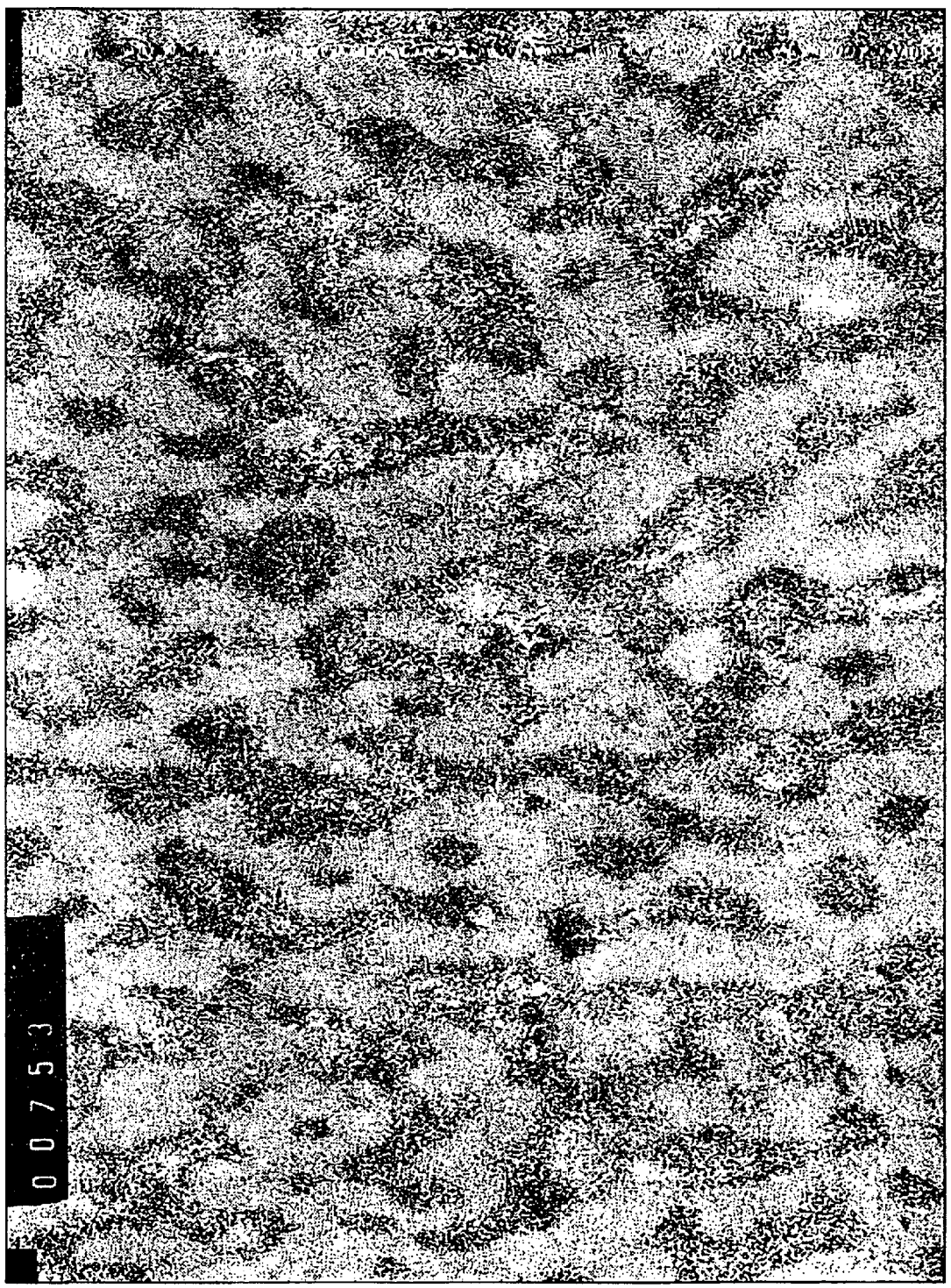
FIG. 2 is a TEM (45000×) of a composition of amorphous polypropylene made by Me$_2$Si(9-Flu)$_2$ZrCl$_2$ and commercial substantial isotactic polypropylene, Moplen Q30P (50/50 wt. %) as described in Comparison Example 15. The dark and bright areas of the picture show the existence of substantially two phases, i.e the components (A) and (B) are less miscible.

The following examples are given for illustrative purposes and are not intended to limit the scope and spirit of the invention.

GENERAL PROCEDURES AND CHARACTERIZATIONS

The following abbreviations are used:

THF=tetrahydrofuran
Et$_2$O=ethyl ether
NaOEt=sodium ethoxide
$^t$BuOK=potassium tert-butoxide
DMSO=dimethyl sulfoxide
DMF=N,N-dimethylformamide
BuLi=butyllithium All operations were performed under nitrogen by using conventional Schlenk-line techniques. Solvents were distilled from blue Na-benzophenone ketyl (Et$_2$O), CaH$_2$ (CH$_2$Cl$_2$), or AliBu$_3$ (hydrocarbons), and stored under nitrogen. BuLi (Aldrich) was used as received.

The $^1$H-NMR analyses of the metallocenes were carried out on a DPX 200 Bruker spectrometer (CD$_2$Cl$_2$, referenced against the middle peak of the triplet of residual CHDCl$_2$ at 5.35 ppm). All NMR solvents were dried over P$_2$O$_5$ and distilled before use. Preparation of the samples was carried out under nitrogen using standard inert atmosphere techniques.

The $^{13}$C-NMR and $^1$H-NMR analyses of the polymers were carried out on a Bruker DPX 400 spectrometer operating at 400.13 MHz and 100.61 MHz respectively. The samples were analyzed as solutions in tetrachlorodideuteroethane at 120° C.

The intrinsic viscosity (I.V.) was measured in tetralin at 135° C.

The melting points of the polymers (Tm) were measured by Differential Scanning Calorimetry (D.S.C.) on an instrument DSC Mettler, according to the following method. About 10 mg of sample obtained from the polymerization were cooled to −25° C. and thereafter heated at 200° C. with a scanning speed corresponding to 20° C. minute. The sample was kept at 200° C. for 5 minutes and thereafter cooled to 0° C. with a scanning speed corresponding to 20° C./minute. Then, a second scanning was carried out with a scanning speed corresponding to 10° C./min. The values reported are those obtained in the second scanning.

The distribution of molecular weights was determined by GPC carried out on an instrument WATERS 150 in orthodichlorobenzene at 135° C.

PREPARATION OF THE METALLOCENES

The synthesis of rac-isopropylidene-bis(3-isopropyl-indenyl)zirconium dichloride (rac-CMe$_2$(3-iPr-Ind)$_2$ZrCl$_2$), rac-isopropylidene-bis(3-methyl-indenyl)zirconium dichloride (rac-CMe$_2$(3-Me-Ind)$_2$ZrCl$_2$), rac-isopropylidene-bis (3-ter-butyl-indenyl)zirconium dichloride (rac-CMe$_2$(3-tBu-Ind)$_2$ZrC$_2$) were carried out as described in WO 96/22995. The synthesis of rac-dimethylsilandiyl-bis(9-fluorenyl) zirconium dichloride (rac-SiMe$_2$(9-fluorenyl)$_2$ZrCl$_2$) was carried out as described in EP-A-0 632 066. The 1:6 rac/meso mixture of dimethylsilanediyl-bis(2-methyl-4-phenyl-indenyl)zirconium dichloride SiMe$_2$ (2-methyl-4-phenyl-indenyl)$_2$ zirconium dichloride was purchased from Boulder Scientific.

Synthesis of 2,2-bis(1-iso-propyl-3-indenyl)propane

Synthesis of 2,2-bis(3-indenyl)propane

Indene (Aldrich, 89.5% by G.C.) was purified by percolation over activated alumina. DMSO (Aldrich, 99%), acetone (99%), KOH and NaOH (Carlo Erba) were used as received.

Synthesis with KOH at Low Temperature 136.8 g of indene (1.054 moli), 1 L of DMSO and 12.5 g of powdery KOH (85%, 189 mmol) were charged under nitrogen in a 1.5 L jacketed reactor equipped with thermometer and magnetic stirring bar. KOH/Indene=0.18.

The dark brown mixture was stirred 15 min at room temperature and then cooled to 12–15° C. Acetone (35 ml, 477 mmol) was added over 30 min with stirring. Acetone/indene=0.45. At the end of the addition, the mixture was stirred at room temperature for 16 h, to give a dark green slightly viscous solution. This solution was poured onto ice containing NH$_4$Cl, then the precipitate was filtered and washed with copious water, then with 1.2 L of cold MeOH. The ochra powdery product was dried in vacuo. 103.7 g of 2,2-bis(3-indenyl)propane (purity 93.3% by G.C.) were obtained. The title product was characterized by means of $^1$H NMR.

Synthesis with Catalytic Amount of KOH 10 g of indene (77 mmol), 80 mL of DMSO and 1 pellet (0.25 g) of KOH (3.8 mmol) were charged under nitrogen in a 250 mL flask equipped with thermometer and magnetic stirring bar. KOH/indene=0.049.

The dark brown mixture was stirred 15 min at 50° C. Acetone (2.56 ml, 35 mmol) was added over 5 min with stirring. Acetone/indene=0.45.

At the end of the addition, the mixture was kept at 50° C. for 6.5 h, the dark green slightly viscous solution was allowed to cool to room temperature and poured onto ice (no NH$_4$Cl added), and a milky suspension is obtained. The precipitate was filtered, the filtrate remain milky, and the rate of filtration is somewhat slower than when NH$_4$Cl is added. Addition of NH$_4$Cl causes separation of more organic product and the water layer becomes more clear (faster filtration rate). The residue was washed with copious water, then with 200 mL of MeOH (at room temperature). The ochra powdery product was dried in vacuo. 6.3 g of 2,2-bis(3-indenyl) propane were obtained (purity 98.8%, isolated yield based on acetone 65.6%).

Synthesis of 2,2-bis(1-iso-propyl-3-indenyl)propane.

4.5 g of 2,2-bis(3-indenyl)propane (purity 94%, 15.53 mmol) were dissolved in 50 mL of anhydrous $Et_2O$ in a 250 mL Schlenk, then cooled to 0° C., 14 mL of 2.5 M BuLi in hexane (35 mmol) were added in 10 min with stirring, then the mixture was allowed to reach room temperature and then stirred for 5 h. After 2 h, a yellow precipitate starts forming. 3.88 mL of iso-propylbromide (41.32 mmol) and 5 mL of $Et_2O$ were added under nitrogen: the yellow precipitate remains. The mixture was stirred for 16 h at room temperature. At the end the so obtained brown suspension was analyzed by G.C.: Low boiling impurities 3.9%, 2,2-bis(3-indenyl)propane 38.3%, medium boiling impurities 1.3%, monoisopropyl derivative 16.4%, product (two isomers) 32.8%, high boiling impurities 7.3%. To the mixture was added additional 11.64 mL of 2-Br-propane (124 mmol) and then refluxed for 7 hours. In 2 hours the mixture turns orange and the suspension gradually dissolves. At the end the solution was cooled and treated with water, the layers were separated, the water layer was extracted twice with $Et_2O$, the organic layers were combined and dried over $Na_2SO_4$, filtered, concentrated in vacuo to yield 5.38 g of orange oil which was analyzed by G.C.: Low boiling impurities 3.9%, 2,2-bis(3-indenyl)propane 0.5%, medium boiling impurities 1.4%, monoisopropyl derivative 6.0%, product (two isomers) 82.5%, high boiling impurities 5.7%. (yield 80% based on the G.C. analysis). The title product was characterized by means of $^1$H NMR.

Synthesis of rac-Methylene-bis(3-t-butyl-1-indenyl) zirconium dichloride a. Synthesis of 3-t-butyl-1-indene 42.0 g of indene (technical grade, 94% by GC, 39.5 g, 340 mmol), 50% wt. aqueous KOH (308 g in 308 mL) and 15.8 g of Adogen (Aldrich, 34 mmol), dissolved in 139.7 g of tert-butylbromide (1019.6 mmol), were introduced in this order, at room temperature, in a 1 L jacketed glass reactor with mechanical stirrer (Büchi). The organic phase turned green. The mixture was heated to 60° C., maintained under vigorous stirring for two hours (a pressure build-up to 2.5 bar-g was observed) and then cooled to room temperature. The total reaction time was 3 hours. The organic phase was extracted with technical hexane (3×200 mL) and analyzed by GC, demonstrating a conversion of 74.5%wt. of 3-tert-butyl-indene and of 1.8% wt. of 1-tert-butyl-indene, the unreacted indene being equal to 13.7% wt. The solution was evaporated under reduced pressure (rotovac) and the resulting dark brown viscous liquid was distilled at 1 mmHg, collecting the fraction boiling between 70 and 80° C. (40 g, 76.8% of 3-tert-butyl-indene and 19.5% of 1-tert-butyl-indene, no indene).

b. Synthesis of bis(1-t-butyl-3-indenyl)methane

In a three neck, 1 L flask with stirring bar were introduced in this order: 10.32 g of $^t$BuOK (92 mmol), 400 mL of DMF, 80.6 g of tert-butyl-indene (98.2% by GC, 460 mmol), obtained as described above, and 18.6 mL of aqueous formalin (37%, 6.9 g, 230 mmol); said reactants were added dropwise over 15 minutes. A mildly exothermic reaction was observed and the solution turned red. The mixture was stirred at room temperature for 2 hours; then the reaction was quenched by pouring the mixture on ice and $NH_4Cl$, extracted with $Et_2O$ (2×250 mL) and concentrated under reduced pressure, thus yielding an orange oily product having the following G.C. composition: 1-$^t$BuInd, 0.3%; 3-$^t$BuInd, 2.8%; bis(1-t-butyl-3-indenyl)methane, 78.3%; the rest being byproducts.

The yield of the raw product was 83.6 g, corresponding to a yield of 79.9%. The orange oily product crystallized upon standing (about 1 hour). The obtained product was further purified by washing with pentane, thus isolating bis(3-tert-butyl-1-indenyl)methane as a light yellow powder, 99.8% pure by G.C.

c. Synthesis of methylenebis(3-t-butyl-1-indenyl) zirconium dichloride 11.0 g of pure bis(1-tert-butyl-3-indenyl)methane (30.9 mmol), obtained as described above, were dissolved in 200 mL $Et_2O$, in a 250 mL Schlenk tube, and the solution was cooled to −15° C. 40 mL of 1.6 M BuLi in hexane (63.3 mmol) were added dropwise, over 15 minutes, under stirring. The solution was allowed to warm to room temperature and stirred for 4.5 hours. An increasing turbidity developed with final formation of a yellow suspension. 7.2 g of $ZrCl_4$ (30.9 mmol) were slurried in 200 mL pentane. The two mixtures were both cooled to −80° C. and the Li salt solution in $Et_2O$ was quickly added to the $ZrCl_4$ slurry in pentane. The cooling bath was removed and after 20 minutes the color of the slurry changed from yellow to red. The reaction mixture was stirred overnight at room temperature and then was brought to dryness under reduced pressure. The red powder was slurried in 200 mL of pentane and transferred into a filtration apparatus equipped with side arm (to allow solvent refluxing) connecting the system above and below the frit, a receiving flask on the bottom and bubble condenser on the top. The red solid was extracted with refluxing pentane for about 3.5 hours. The filtrate was evaporated to dryness under reduced pressure to give a red paste which contained rac-$CH_2(3-^tBu-1-Ind)_2ZrCl_2$ free from its meso isomer, but containing polymeric byproducts. The paste was washed twice with $Et_2O$ (20+10 mL) to give 1 g of pure product. The red solid on the frit was further extracted with $CH_2Cl_2$ until the filtrate was light orange (6 hours) and dried. $^1$H-NMR analysis showed the presence of pure rac-$CH_2(3-^tBu-Ind)_2ZrCl_2$ (7.25 g).

The total yield (8.25 g of red powder) of rac-$CH_2(3-^tBu-Ind)_2ZrCl_2$ was 52%.

$^1$H NMR($CDCl_3$, δ, ppm): s, 1.41, $^tBu$, 18H; s, 4.78, $CH_2$, 2H; s, 5.79, 2H, Cp-H; m, 7.15, 2H, m, 7.36, 2H; m, 7.47, 2H; m, 7.78, 2H.

Synthesis of methylene-bis(3-iso-propyl-1-indenyl)$ZrCl_2$ a. Synthesis of 3-iso-propyl-1-indene 25 g of indene (Aldrich, 94.4%) in 140 mL $Et_2O$ were placed in a 0.5 L flask and cooled to −20° C.; 141 mL of n-BuLi (1.6 M in hexane, 226 mmol) were added dropwise in about 30′. The reaction mixture was allowed to warm to room temperature and then stirred for 5 hours (brown-orange solution). This solution was then slowly added to a solution of 101 mL of i-PrBr (Aldrich, MW 123 g/mol, d=1.31 g/mL, 1.07 mol) in 140 mL $Et_2O$ maintained at 0° C. The reaction was allowed to proceed with stirring at room temperature for 72 hours. The mixture was poured onto 300 g of ice, the water layer was extracted with $Et_2O$ (3×200 mL) and the $Et_2O$ wash combined with the organic layer, dried over $MgSO_4$ and after filtration the solvent was removed under vacuum to leave 30.9 g of a yellow oil (yield based on GC analysis is 62%). 18 g of this oil was distilled (adding NaOH pellets to avoid polymerization, with a 20 cm vigreux column) collecting the fraction boiling at 95–105° C. at 10 mmHg, 10 g, GC: i-PrInd (2 isomers)=92.1%, $^1$H NMR ($CDCl_3$, d, ppm): d, 1.45, 1.47, 6H; m, 3.47, CH, 1H; s, 3.47, 2H, $CH_2$; s, 6.35, 1H,; m, 7.47, 2H; m, 7.3–7.7, 4H. Major isomer is 3-i-Pr-indene.

b. Synthesis of bis(iso-propyl-indenyl)methane

In a three neck, 500 mL flask with stirring bar were introduced in this order: 10 g of i-Pr-indene (92%, MW 158, 58.3 mmol) dissolved in 250 mL of DMSO, and 1.42 g of t-BuOK (MW 112.82. 12.6 mmol). The yellow solution turns green. 2.56 mL of aqueous formalin (37%, MW 30.03, 31.6 mmol) in 70 mL of DMSO were added in 15'. A mildly hexothermic reaction is observed and the solution turns dark brown. At the end of the addition the reaction mixture was stirred for 16 h at room temperature.

The reaction was quenched by pouring the mixture on 200 g ice with 0.3 g $NH_4Cl$. The organic product was extracted with $Et_2O$, the water layer was washed with $Et_2O$ (3×100 mL), the organic layers combined, dried over $MgSO_4$, filtered and concentrated to leave 13.65 g of yellow oil, which contains 32% of the desired product by GC analysis.

c. Synthesis of methylenebis(3-iso-propyl-indenyl)$ZrCl_2$ 13.6 g of raw bis(3-iso-propyl-1-indenyl)methane were dissolved in 200 mL $Et_2O$ in a 250 mL Schlenk tube, and the solution cooled to −80° C. 33.3 mL of 2.5 M BuLi in hexane (83.2 mmol) were added dropwise over 15 min with stirring. The solution is allowed to warm to room temperature and stirred for 5 hours. An increasing turbidity develops with final formation of an orange precipitate. $Et_2O$ was removed under vacuum and 200 mL of toluene were added. 9.7 g of $ZrCl_4$ (MW 233.03, 41.62 mmol) were slurried in 200 mL of toluene. The two mixtures were both cooled to −80° C. and the $ZrCl_4$ slurry in toluene was quickly added to the Li salt solution in toluene. The cooling bath is removed. The reaction mixture is stirred overnight at room temperature. Filtration: the residue was a sticky glue (eliminated). The filtrate was evaporated to 25 mL under reduced pressure: the solid precipitated was isolated by filtration. The title compound was characterized by $^1H$ NMR.

POLYMERIZATION

Methylalumoxane (MAO)

A commercial (Witco) 10% toluene solution was dried in vacuo until a solid, glassy material was obtained which was finely crushed and further treated in vacuo until all volatiles were removed (4–6 hours, 0.1 mmHg, 50° C.) to leave a white, free-flowing powder.

Preparation of the Cocatalyst

The catalyst mixture was prepared by dissolving the desired amount of the metallocene with the proper amount of the MAO solution, obtaining a red solution, which was stirred for 10 min at ambient temperature and then injected into the autoclave at the polymerization temperature in the presence of the monomer.

Propylene Homopolymerization

EXAMPLES 1–6 AND COMPARATIVE EXAMPLES 8–10

Propylene was charged at room temperature in a 1-L jacketed stainless-steel autoclave, equipped with magnetically driven stirrer and a 35-mL stainless-steel vial, connected to a thermostat for temperature control, previously purified by washing with a TIBA solution in hexane and dried at 50° C. in a stream of propylene. $AliBu_3$ (1 mmol in hexane) was added as scavenger before the monomer. The autoclave was then thermostated at 2° C. below the polymerization temperature, and then the toluene solution containing the catalyst/cocatalyst mixture was injected in the autoclave by means of nitrogen pressure through the stainless-steel vial, the temperature rapidly raised to the polymerization temperature and the polymerization carried out at constant temperature for 1 hour. After venting the unreacted monomer and cooling the reactor to room temperature, the polymer was dried under reduced pressure at 60° C.

The polymerization conditions are reported in Table 1.

The characterisation data of the obtained polymers are shown in table 2.

EXAMPLE 7

The polymerization was carried out as above described, except that a 4 L autoclave was used and the polymerization time was 2 hours.

The polymerization conditions are reported in Table 1.

The characterisation data of the obtained polymer are shown in table 2.

Propylene/ethylene copolymerization

EXAMPLES 11–13

The copolymerizations were carried out in a 2.6 L jacketed stainless-steel autoclave as described above. $AliBu_3$ (1 mmol in hexane) and propylene (530 g, 1 L total volume at 60° C.) were charged and thermostatted at 55° C., the catalyst/cocatalyst mixture was injected in the autoclave by means of ethylene pressure (using the amount of ethylene required to achieve the bath composition shown in Table 5) through the stainless-steel vial, the temperature rapidly raised to 60° C. and the polymerization carried out at constant temperature and monomer composition, by feeding a mixture of ethylene and propylene 5/95 by weight (Examples 9 and 10) or 3/97 by weight (Example 11). The polymerizations were stopped with CO, the not consumed monomers vented, and the polymer dried under reduced pressure at 60° C.

The polymerization conditions are reported in Table 3.

The characterisation data of the obtained copolymers are shown in table 4.

Preparation of the Compositions

EXAMPLE 14

20 g of a propylene polymer obtained according to Example 3 [component (A)], the same amount of Moplen Q30P (a commercial isotactic polypropylene made by Montell) [component (B)], and 0.1 wt % of IRGANOX B215 (a commercial stabilizer provided by the Ciba company) were mixed in a Banbury at 200° C. for 10 min at 50 rpm. The blend obtained thereof was compression moulded into plaques of 1 mm thickness at 200° C. for 5 min and subsequently cooled in a water cooled press. The characteristic of the obtained composition is illustrated in Table 5.

EXAMPLE 15 (COMPARISON)

The example was carried out according to example 14, with the exception that a polypropylene obtained with $SiMe_2(9$-fluorenyl$)_2ZrCl_2$ was used as component (A). The characteristic of the obtained composition is illustrated in Table 5.

The beneficial characteristic of the composition according to the present invention is illustrated in Table 5 by the inferior haze value of the composition according to Example 14 with regard to the composition according to the comparison example 15.

EXAMPLE 16 (COMPARISON)

A propylene polymerization was carried out according to the procedure described in examples 1–6 but using 0.5 mg of a 1:6 rac/meso mixture of $SiMe_2(2\text{-methyl-4-phenyl-indenyl})_2ZrC_2$ in the presence of 100 ml $H_2$. The polymerization conditions are reported in Table 1. The characteristic of the obtained composition is illustrated in Table 5.

TABLE 1

| Example | zirconocene dichloride type | mg | Al/Zr (mol) | Tp (° C.) | yield (g) | activity (Kg/g$_{cat}$ · h) |
|---|---|---|---|---|---|---|
| 1 | $CMe_2(3\text{-iPr-Ind})_2$ | 3 | 1000 | 20 | 33 | 10.8 |
| 2 | " | 2 | 1000 | 30 | 68 | 33.9 |
| 3 | " | 2 | 1000 | 45 | 74 | 36.9 |
| 4 | " | 1 | 1000 | 50 | 36 | 35.8 |
| 5 | " | 1 | 1000 | 60 | 62 | 61.9 |
| 6 | $CH_2(3\text{-iPr-Ind})_2$ | 0.8 | 1000 | 50 | 42 | 52 |
| 7 | " | 5 | 3000 | 40 | 830 | 83 |
| 8 (comp) | $CMe_2(3\text{-Me-Ind})_2$ | 1 | 1000 | 50 | 10 | 10 |
| 9 (comp) | $CMe_2(3\text{-tBu-Ind})_2$ | 0.5 | 5000 | 50 | 37.6 | 75.3 |
| 10 (comp) | $CH_2(3\text{-tBu-Ind})_2$ | 2.0 | 1000 | 50 | 144.7 | 72.3 |
| 16 (comp) | $SiMe_2(2\text{-methyl-4-phenyl-indenyl})_2$ | 0.5 | 1000 | 60 | 49.38 | n.d. |

TABLE 2

| Example | zirconocene dichloride | Exp. Triad Distribution % mm | rm | rr | I.V dl/g | Tg ° C. |
|---|---|---|---|---|---|---|
| 1 | $CMe_2(3\text{-iPr-Ind})_2$ | 36.7 | 39.4 | 23.9 | 2.24 | −0.3 |
| 2 | " | 35.6 | 39.6 | 24.8 | 2.27 | 1.0 |
| 3 | " | 33.9 | 40.9 | 25.2 | 1.55 | n.d. |
| 4 | " | 32.2 | 40.5 | 27.3 | 1.54 | n.d. |
| 5 | " | 30.3 | 42.7 | 27.0 | 0.87 | n.d. |
| 6 | $CH_2(3\text{-iPr-Ind})_2$ | 52.9 | 30.5 | 16.6 | 0.9 | n.d. |
| 7 | " | 55.5 | 28.4 | 16.1 | 1.17 | −9 |
| 8 (comp) | $CMe_2(3\text{-Me-Ind})_2$ | n.d. | n.d. | n.d. | oil | n.d. |
| 9 (comp) | $CMe_2(3\text{-tBu-Ind})_2$ | 96.8 | 2.1 | 1.1 | 0.89 | n.d |
| 10 (comp) | $CH_2(3\text{-tBu-Ind})_2$ | 98.2 | 1.2 | 0.6 | 1.59 | n.d | n.d. not determined

TABLE 3

| Example | zirconocene dichloride type | mg | Al/Zr (mol) | liquid phase ethylene % wt | Tp (° C.) | yield (g) | activity (Kg/g$_{cat}$ · h) |
|---|---|---|---|---|---|---|---|
| 11 | $CMe_2(3\text{-iPr-Ind})_2$ | 2 | 1000 | 0.82 | 60 | 94 | 94 |
| 12 | $CMe_2(3\text{-iPr-Ind})_2$ | 2 | 1000 | 0.4 | 60 | 126 | 126 |
| 13 | $CMe_2(3\text{-iPr-Ind})_2$ | 2 | 1000 | 0.2 | 60 | 55 | 55 |

TABLE 4

| Ex. | zirconocene dichloride | liquid phase ethylene % wt | ethylene (% wt) | N.M.R. PEP (% mols) | EEE | EEP | PEP/(PEP + EEP + EEE) | I.V. (dl/g) | Tg (° C.) |
|---|---|---|---|---|---|---|---|---|---|
| 11 | $CMe_2(3\text{-iPr-Ind})_2$ | 0.82 | 13.8 | 0.171 | 0 | 0.022 | 0.89 | 0.60 | −19.8 |
| 12 | " | 0.4 | 7.7 | 0.104 | 0 | 0.007 | 0.94 | 0.67 | −13.5 |
| 13 | " | 0.2 | 9.9 | 0.130 | 0 | 0.011 | 0.91 | 0.63 | −15.8. |

TABLE 5

| Example | zirconocene | I.V. (dl/g) Component (A) | I.V. (dl/g) Component (B) | (A)/(B) (wt/wt) | $^{13}$C-NMR of component (A) Pentads mmmm | mmmr | rrrr | mmmm/ rrrr | mmmm/ mmmr | Haze (%) |
|---|---|---|---|---|---|---|---|---|---|---|
| 14 | $CMe_2(3\text{-iPr-Ind})_2$ | 1.55 | 2.6 | 50/50 | 14.80 | 14.24 | 6.41 | 2.31 | 1.04 | 61 |
| 15 (comp) | $SiMe_2(9\text{-Flu})_2$ | 1.49 | 2.6 | 50/50 | | | | | | 76 |
| 16 (comp) | $SiMe_2(2\text{-methyl-4-phenyl-indenyl})_2$ | 1.05 | 6.8 | 40/60 | 10.25 | 16.47 | 2.79 | 3.67 | 0.62 | |

What is claimed is:

1. A process for the preparation of a compound of formula (II):

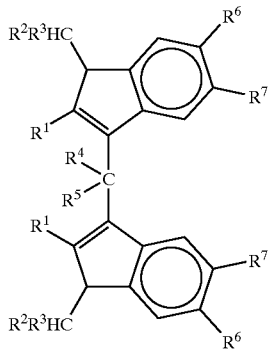

(II)

wherein substituents R1 are hydrogen atoms;
the $R^2$ and $R^3$ substituents are, independently from each other, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals. optionally containing silicon or germanium atoms, or where $R^2$ and $R^3$ can be joined together to form a 4 to 6 membered ring or a 6 to 20 fused ring system;
the $R^4$ and $R^5$ substituents, same or different, are hydrogen atoms or —$CHR^8R^9$ groups, and $R^4$ and $R^5$ can form a ring having 3 to 8 carbon atoms which can contain hetero atoms;
the $R^6$ and $R^7$ substituents, same or different, are hydrogen, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms; and optionally two adjacent $R^6$ and $R^7$ substituents can form a ring comprising from 5 to 8 carbon atoms;
the $R^8$ and $R^9$ substituents, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, which can form a ring having 3 to 8 carbon atoms which can contain hetero atoms,
and/or its double bond isomers
comprising the following steps:
a) contacting a compound of formula (III):

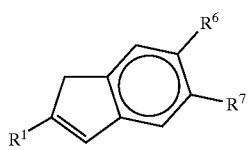

(III)

and/or its double bound isomer
with a base selected from the group consisting of alkali and earth alkali metal hydroxides or alkoxides in the presence of dimethylsulfoxide or 1-Me-2-pyrrolidinone, thereby forming a corresponding anionic form of formula (III);

b) treating the corresponding anionic form of formula (III) with a compound of general formula $R^4R^5CO$, in order to obtain a compound of the formula (IV):

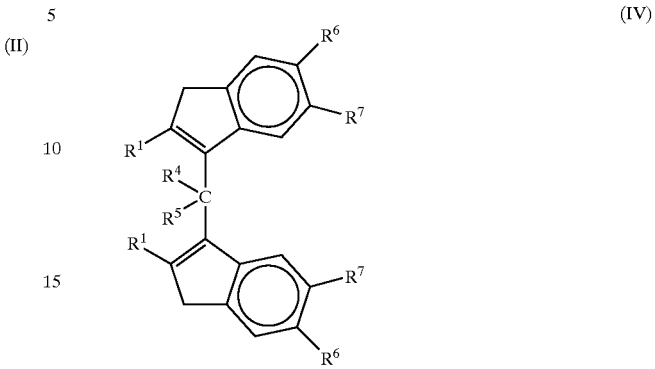

(IV)

c) contacting the compound of formula (IV) with a base, wherein the molar ratio between the base and the compound of formula (IV) is equal to or greater than 2, thereby forming a corresponding di-anionic form of formula (IV);
d) treating the corresponding di-anionic form of formula (IV) with a compound of formula (V) $CHR^2R^3L$, wherein L is a halogen atom selected from the group 17 of the Periodic Table of the Elements, and the molar ratio between the compound (V) and the corresponding di-anionic form of formula (IV) is equal to or greater than 2.

2. The process according to claim 1, wherein the base used in step a) is sodium or potassium hydroxide, and the molar ratio between said base and the compound of formula (III) is in the range from 0.01 to 1.

3. The process according to claim 1, wherein L is selected from chlorine, bromine, iodine and fluorine.

4. The process according to claim 3, wherein L is bromine.

5. The process according to claim 4, wherein the base used in step c) is selected from alkali and earth alkali metal hydroxides, organic lithium compounds and metallic sodium or potassium.

6. The process according to claim 5, wherein the base is buthyllithium.

7. A process for the preparation of a compound of formula (II):

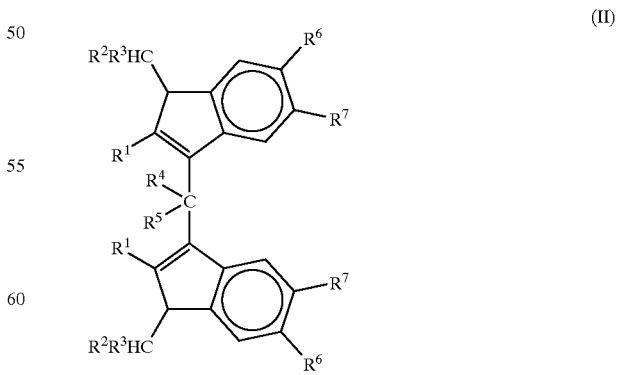

(II)

wherein substituents $R^1$ are hydrogen atoms;
the $R^2$ and $R^3$ substituents are, independently from each other, $C_1$–$C_{20}$-alkyl, $C_3$–$C_{20}$-cycloalkyl, $C_2$–$C_{20}$- alkenyl, $C_6$–$C_{20}$-aryl, $C_7 \geq C_{20}$-alkylaryl or $C_7$–$C_{20}$-arylalkyl radicals, optionally containing silicon or germanium atoms, or where $R^2$ and $R^3$ can be joined together to form a 4 to 6 membered ring or a 6 to 20 fused ring system;

the $R^4$ and $R^5$ substituents, same or different, are hydrogen atoms or —$CHR^8R^9$ groups, and $R^4$ $R^5$ can form a ring having 3 to 8 carbon atoms which can contain hetero atoms;

$R^6$ $R^7$ substituents, same or different, are hydrogen, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms; and optionally two adjacent $R^6$ and $R^7$ substituents can form a ring comprising from 5 to 8 carbon atoms;

the $R^8$ and $R^9$ substituents, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, which can form a ring having 3 to 8 carbon atoms which can contain hetero atoms, and/or its double bond isomers comprising the following steps:

a) contacting a compound of formula (III):

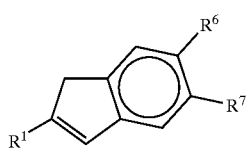

(III)

and/or its double bound isomer with a base selected from the group consisting of sodium hydroxide and potassium hydroxide, in the presence of an oxygen containing solvent, wherein the molar ratio between the base and the compound of formula (III) is in the range from 0.01 to 1, thereby forming a corresponding anionic form of formula (III);

b) treating the corresponding anionic form of formula (III) with a compound of general formula $R^4R^5CO$, in order to obtain a compound of the formula (IV):

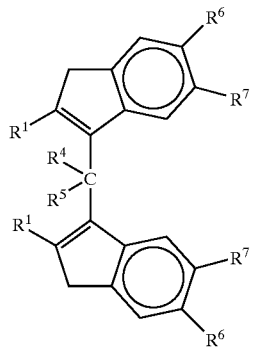

(IV)

c) contacting the compound of formula (IV) with a base, wherein the molar ratio between the base and the compound of formula (IV) is equal to or greater than 2, thereby forming a di-anionic form of formula (IV);

d) treating the corresponding di-anionic form of formula (IV) with a compound of formula (V) $CHR^2R^3L$, wherein is a halogen atom selected from the group 17 of the Periodic Table of the Elements, and the molar ratio between the compound (V) and the corresponding di-anionic form of formula (IV) is equal to or greater than 2.

8. The process according to claim 7, wherein L is selected from chlorine, bromine, iodine and fluorine.

9. The process according to claim 8, wherein L is bromine.

10. The process according to claim 9, wherein the base used in step c) is selected from alkali and earth alkali metal hydroxides, organic lithium compounds and metallic sodium or potassium.

* * * * *

UNITED STATES PATENT AND TRADEMARK OFFICE
CERTIFICATE OF CORRECTION

PATENT NO. : 6,844,288 B2
DATED : January 18, 2005
INVENTOR(S) : Luigi Resconi et al.

It is certified that error appears in the above-identified patent and that said Letters Patent is hereby corrected as shown below:

Column 25,
Line 1, change "$C_7 \geq C_{20}$ alkylaryl" to -- $C_7\text{-}C_{20}$ alkylaryl --.

Signed and Sealed this

Twenty-fourth Day of May, 2005

JON W. DUDAS
*Director of the United States Patent and Trademark Office*